United States Patent
Ohara et al.

(10) Patent No.: US 7,184,516 B2
(45) Date of Patent: Feb. 27, 2007

(54) DIGITAL PHASE CONTRAST X-RAY RADIOGRAPHING SYSTEM

(75) Inventors: Hiromu Ohara, Hachioji (JP); Chika Honda, Hachioji (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 10/318,660

(22) Filed: Dec. 12, 2002

(65) Prior Publication Data

US 2003/0123611 A1 Jul. 3, 2003

(30) Foreign Application Priority Data

Dec. 21, 2001 (JP) .............................. 2001-389518

(51) Int. Cl.
*G01N 23/04* (2006.01)

(52) U.S. Cl. .......................................... 378/62; 378/70

(58) Field of Classification Search ............... 378/98.4, 378/98.8, 108, 115, 116, 62, 72, 87, 36, 95, 378/70

See application file for complete search history.

(56) References Cited

U.S. PATENT DOCUMENTS

| 5,657,362 | A | * | 8/1997 | Giger et al. | 378/37 |
| 5,812,629 | A | * | 9/1998 | Clauser | 378/62 |
| 6,018,564 | A | * | 1/2000 | Wilkins | 378/62 |
| 6,035,013 | A | * | 3/2000 | Orava et al. | 378/37 |
| 6,404,848 | B1 | * | 6/2002 | Ishisaka et al. | 378/62 |
| 6,628,815 | B2 | * | 9/2003 | Wang | 382/132 |

* cited by examiner

*Primary Examiner*—Edward J. Glick
*Assistant Examiner*—Hoon Song
(74) *Attorney, Agent, or Firm*—Squire, Sanders & Dempsey L.L.P.

(57) ABSTRACT

An X-ray image radiographing system for radiographing a subject is provided with an X-ray source to emit X-rays; a digital X-ray detector to detect a digital X-ray image of the subject, wherein the subject is placed between the X-ray source and the digital X-ray detector in an arrangement to satisfy the following formulas so that an edge of the digital X-ray image is enhanced oven an edge-enhanced width: 0.1 m$\leq$R1$\leq$10 m, and 0.15 m$\leq$R2$\leq$10 m, where R1 is a distance between the X-ray tube and the subject and R2 is a distance between the subject and the digital X-ray detector. The digital X-ray detector has a pixel size almost equal to the half of the edge-enhanced width.

7 Claims, 7 Drawing Sheets the width of the enhanced edge portion

DIGITAL PHASE CONTRAST X-RAY RADIOGRAPHING SYSTEM

BACKGROUND OF THE INVENTION

The present invention relates to an X-ray radiographing system used for non-destructive tests and medical image diagnoses, and in particular, to a digital phase contrast X-ray radiographing system capable of obtaining X-ray images having high sharpness and high image quality.

X-ray penetrates material, and when X-ray penetrates material, the X-ray is absorbed by photoelectric effect and Compton scattering performed by an atom of which the material is composed. The absorption amount of X-ray depends upon an atomic weight. Accordingly, after X-ray penetrates the material, X-ray image is obtained by the acquisition of the X-ray intensity distribution that is two-dimensional, based on the distribution of the atom. The X-ray intensity difference generated as an image density obtained here is called absorption contrast generally. Since the discovery of X-ray by Dr. Roentgen in 1895, this is the principle used as X-ray image.

On the other hand, in the 1990s, the research about the phase contrast X-ray image started widely. X-ray has a nature that is the same as that of light, because X-ray is an electromagnetic wave. That is, refraction and interference are generated. The X-ray intensity difference obtained by this nature is called the phase contrast. It was found that the edge of the absorption contrast image in the past is depicted sharply by the phase contrast. However, as compared with visual rays, a refractive index of X-ray is extremely small, the phase contrast image was not observed in the conventional X-ray radiographing method. Further, since the wavelength of the X-ray is shorter than that of the visual rays by about three figures, it is extremely difficult to obtain the phase contrast image by controlling interference, and at present, a stage is for research, and not a stage of its wide use in hospital.

There is reported the methods in which a sharp X-ray image is obtained by acquiring an edge-enhanced image that is so-called the one having enhanced edge of the image, using the nature of refraction of X-ray. That is, there is the journal of Medical Physics, page 2190, issue 10, volume 26 by Mr. N. Yagi, for the case that radiation X-ray from synchrotron is used, for example, and further, there is the journal of the Optical Review, page 566, issue 6, volume 7 (1999) by Mr. A. Ishisaka, for the case Coolidge X-ray tube (electro-thermal X-ray tube) is used. Concerning the methods for obtaining a phase contrast X-ray image that is edge-enhanced by using interference of X-ray, there is the journal of Nature, page 335, volume 384 (1996), by S. W. Wilkins, or an official report of Patent WO96/31098, for the case that a special Coolidge X-ray tube having microscopic size of focal spot is used, or there is disclosed on the official report of TOKKAIHEI 9-187455, for the case that the principle of an interferometer is applied by using the above-mentioned radiation X-ray.

This invention is the one relating to the X-ray radiographing system that can obtain X-ray image having high sharpness, using the refraction of X-ray. To radiograph the sharp X-ray image by refraction, there are used a non-screen X-ray film, one in which X-ray intensifying screen and X-ray film are used, or a very small CCD camera whose pixel size is about 10 μm. The foregoing is because it has been thought that very high resolving power is necessary for radiographing the enhanced edge formed by the refraction of X-ray.

Here, in the case of a non-screen X-ray film, or in the case of one in which X-ray intensifying screen and X-ray film are used, the resolving power is very high, however, they are so-called analog X-ray image detector, and it is impossible to perform freely image processing or magnification/reduction of output image.

Further, in order to obtain a digital X-ray image, it is possible to use X-ray detector by using CCD having high resolving power, but CCD section is required to be cooled to keep sufficient sensitivity, and the apparatus turns out to be very expensive, and due to this, it is used only for the particular research in a limited area.

SUMMARY OF THE INVENTION

The invention is the one which provides the digital phase contrast X-ray radiographing system that is able to obtain the digital image of the phase contrast X-ray image conveniently. That is, the invention provides the digital phase contrast X-ray radiographing system that obtains the digital X-ray phase contrast image having the high sharpness easily, using the digital X-ray image detector such as a computed radiography (CR), or a flat type X-ray picture image detector (FPD), used widely in medical field or non-destructive test.

In order to solve the above-mentioned subject and accomplish the purpose, the invention is structured as follows.

Structure (1) A digital phase contrast X-ray radiographing system having therein a digital X-ray image detector for obtaining a digital image of a phase contrast X-ray image, wherein a pixel size of the digital X-ray image detector is nearly equal to a half-width of phase contrast edge-enhancement of the phase contrast X-ray image.

Structure (2) The digital phase contrast X-ray radiographing system described in Structure (1), wherein X-ray used is generated by a Coolidge X-ray tube.

Structure (3) The digital phase contrast X-ray radiographing system described in Structure (1), wherein there is used a digital X-ray image detector having a pixel size of 0.5 to 3 times value of EB obtained by the following simulation formula.

$$EB=2.3(1+R2/R1)^{1/3}\{R2\delta(2r)^{1/2}\}^{2/3}+D\times(R2/R1)$$

Structure (4) The digital phase contrast X-ray radiographing system described in Structure (3), wherein E value obtained by the following simulation formula is not smaller than 12 μm and not larger than 300 μm.

$$E=2.3(1+R2/R1)^{1/3}\{R2\delta((2r)^{1/2}\}^{2/3}$$

Structure (5) The digital phase contrast X-ray radiographing system described in Structure (1), wherein X-ray used is a radiation X-ray.

Structure (6) The digital phase contrast X-ray radiographing system described in Structure (5), wherein a digital X-ray image detector having a pixel size of 0.5 to 3 times EP value obtained by the following simulation formula is used.

$$EP=2.3\{R2\delta(2r)^{1/2}\}^{2/3}$$

Structure (7) The digital phase contrast X-ray radiographing system described in Structure (1), wherein a pixel size is not smaller than 20 μm and not larger than 300 μm.

Structure (8) The digital phase contrast X-ray radiographing system described in Structure (1), wherein a size of a detection surface of the digital X-ray picture image detector is not smaller than 15 cm×15 cm, and not larger than 90 cm×90 cm.

DETAILED DESCRIPTION OF THE PREFERRED EMBODIMENT

The structures of the invention will be described in detail below.

Figure 1:
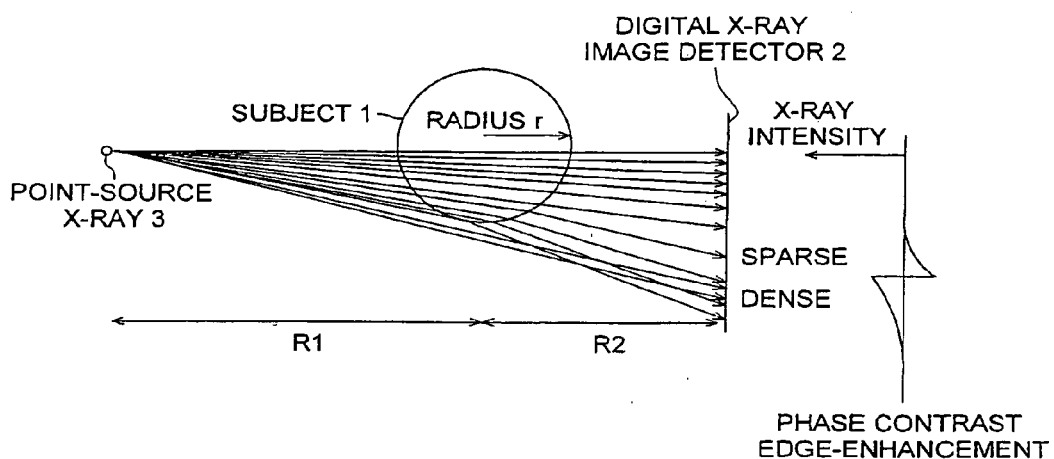
FIG. 1 is a drawing showing the principle wherein a phase contrast edge-enhancement of the subject image is generated by refraction of the X-ray.

FIG. 1 shows the principle, wherein the phase contrast edge-enhancement of the subject image is generated by refraction of the X-ray. Since the refractive index of X-ray is smaller than one, when X-ray penetrates the subject 1 composed of a columnar or spherical shaped object, the columnar or spherical shaped object works as a concave lens. That is, X-ray having penetrated the edge of the object overlaps X-ray having penetrated side of the object, on digital X-ray picture image detector 2, and thereby the intensity of X-ray increases. Since X-ray penetrates the edge of the object and is forced out to the outside of the object, the intensity of X-ray decreases in the vicinity of the edge of the object. Due to the foregoing, the intensity of X-ray causes a peak on the outer side and a trough on the inner side, on the boundary of the edge of the object. The function of the edge-enhancement mentioned above is called an edge effect. Accordingly, when phase contrast edge-enhancement by refraction of X-ray is generated, X-ray image having high sharpness with sharply described edge can be obtained.

Figure 2:
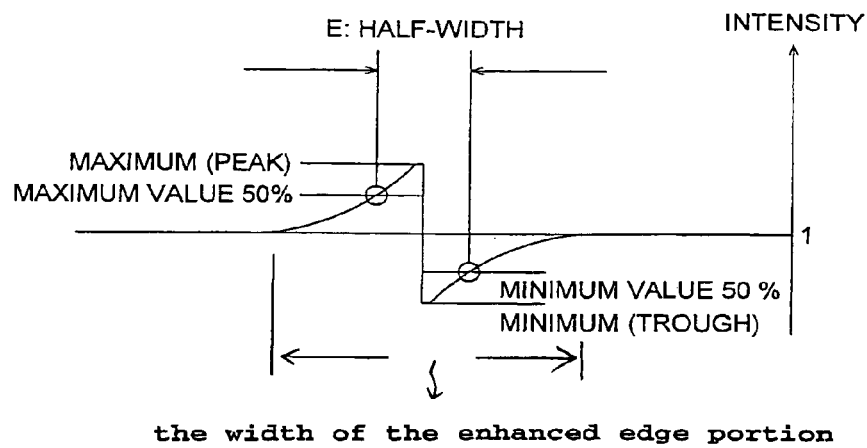
FIG. 2 is a drawing showing a half-width of a phase contrast edge-enhancement.

When X-ray source is regarded as a point light source, half-width E of the phase contrast edge-enhancement can be shown by the following formula, as shown in FIG. 2.

$$E=2.3(1+R2/R1)^{1/3}\{R2\delta((2r)^{1/2})^{2/3} \quad (1)$$

Here, R1 represents a distance between X-ray point source 3 and a center of a column of the subject 1, R2 represents a distance between a center of a column that is assumed as the subject 1 and digital X-ray image detector 2, r corresponds to a radius of the subject 1 that is assumed as the column. Since a blood vessel or a bone is a main substance to constitute the X-ray image in a human body, a style of the human body can be approximated to the column approximately. Further, concerning δ, when refraction index n of X-ray is expressed as follows, $$n=1-\delta \quad (2)$$

δ is one that relates to a phase change.

Figure 3:
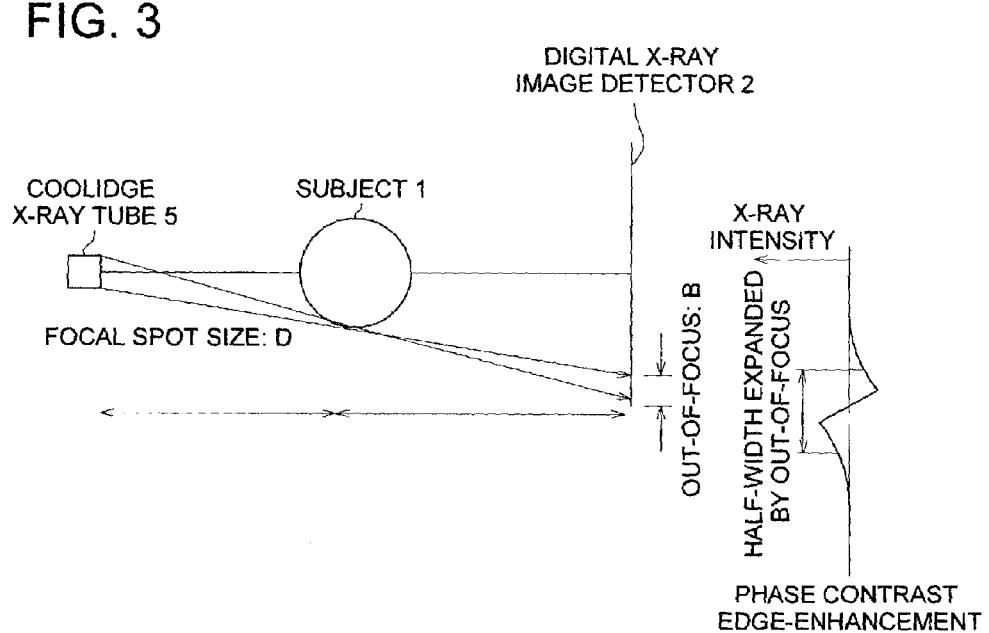
FIG. 3 is a drawing showing a half-width of a phase contrast edge-enhancement in case of using a Coolidge X-ray tube.

Here, in medical field or non-destructive test, the Coolidge X-ray tube (or electro-thermal X-ray tube) 5 is widely used. The case in which the Coolidge X-ray tube 5 is used is shown in FIG. 3. In the Coolidge X-ray tube 5, a thermal electron collides with a metal anode such as tungsten to radiate X-ray, and X-ray flies out radially from a nearly square window called a focal spot. A length of a side of the nearly square window is called a focal spot size. When the Coolidge X-ray tube 5 is used, the X-ray source cannot be regarded as an ideal point-source light. That is, the half-width of the phase contrast edge-enhancement is extended by the focal spot as the X-ray source having a finite size, or a so-called geometrical unsharpness, and further, the intensity is decreased. In this case, the half-width of the phase contrast edge-enhancement is expressed by formula (3).

$$BE=2.3(1+R2/R1)^{1/3}\{R2\delta(2r)^{1/2}\}^{2/3}+D\times(R2/R1) \quad (3)$$

Here, D shows a size of focal spot of the Coolidge X-ray tube 5 used.

Figure 4:
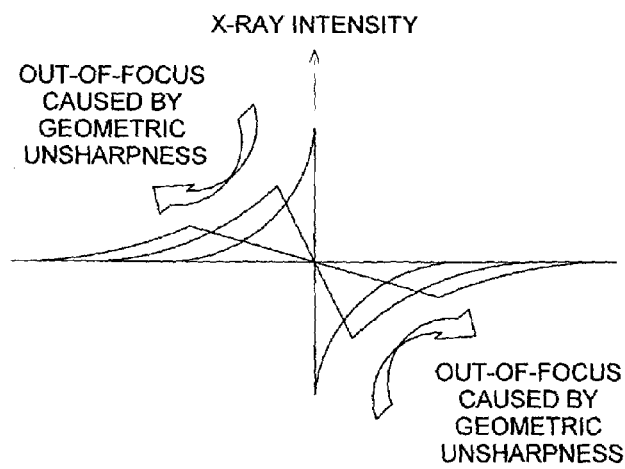
FIG. 4 is a drawing illustrating that the edge-enhancement is detectable even when a pixel size of a digital X-ray image detector has a fixed size.

That is, inversely, since the half-width of the phase contrast edge-enhancement is expanded by this geometrical unsharpness, a detectable range of the edge-enhancement can be expanded, as shown in FIG. 4, though the pixel size of the digital X-ray image detector 2 has a fixed size. This is a fundamental principle of the present invention, when the Coolidge X-ray tube 5 is used.

Next, Spring-8 in Harima, Hyougo Prefecture or radiation X-ray apparatus of High Energy Research in Tukuba, Ibaraki Prefecture, can obtain a strong X-ray beam which is exceedingly near a parallel ray. The parallel X-rays can be regarded as an occasion wherein the point-source light or the X-ray focal spot having the definite size is brought to the infinite distance. That is, R1 is determined to be infinite in the formula (1) or (3), the half-width EP of the phase contrast edge-enhancement using a parallel X-ray is expressed in formula (4).

$$EP=2.3\times\{R2\delta(2r)^{1/2}\}^{2/3} \quad (4)$$

Figure 5:
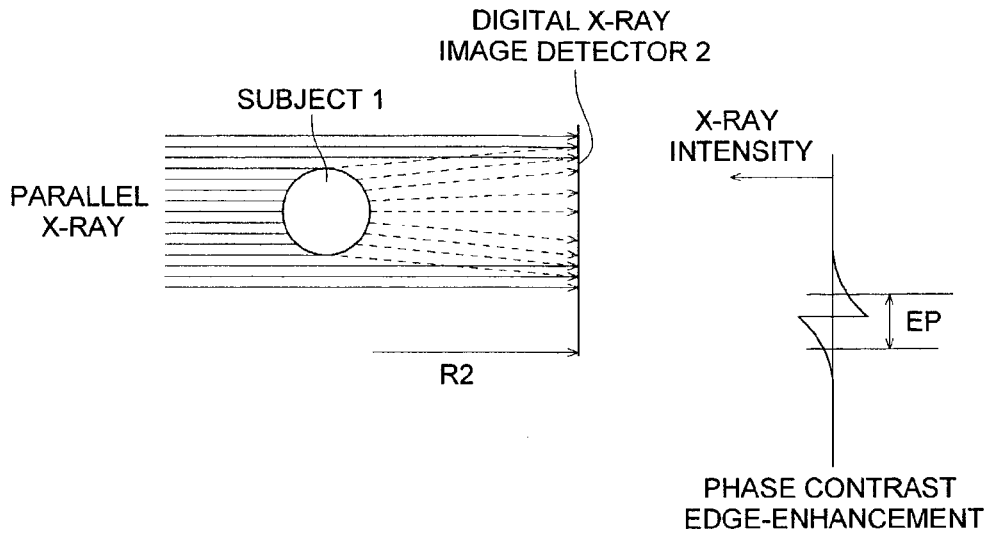
FIG. 5 is a drawing describing EP which is expanded so that a phase contrast edge-enhancement is observed by a digital X-ray image detector having a fixed size of pixel, using a parallel X-ray source.

To observe the phase contrast edge-enhancement on the digital X-ray image detector 2 having the fixed sized pixel, using a parallel X-ray source, the expansion of EP is realized by the enlargement of R2, as shown in FIG. 5. When the parallel X-ray is used, the reduction of the X-ray intensity does not occur, even though the digital X-ray image detector 2 is moved away from the subject 1. Accordingly, by the establishment of R2 having the sufficient length, the phase contrast edge-enhancement can be observed by the digital X-ray image detector 2 having large pixels.

Figure 6:
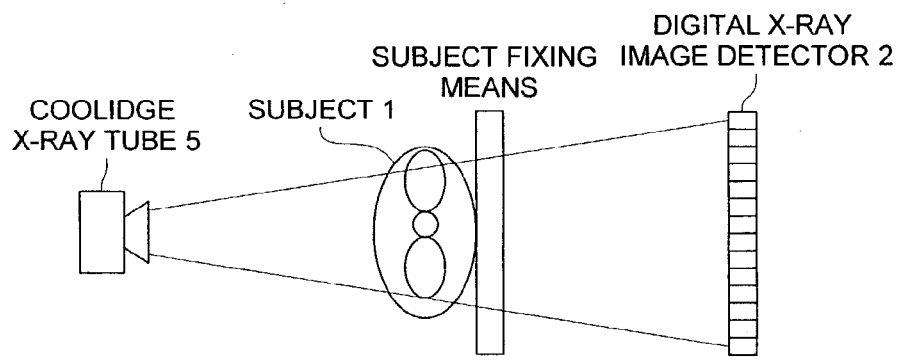
FIGS. 6(*a*) and 6(*b*) each is a drawing describing that a digital X-ray image detector is composed of pixels which are squares or rectangles.
Figure 6:
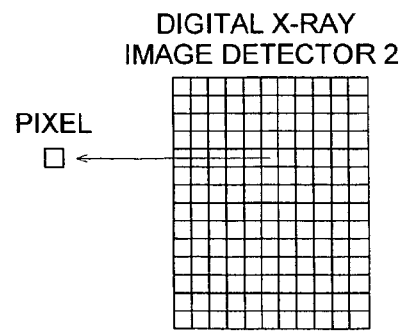

In the digital X-ray radiographing, the digital X-ray image detector 2 for a two-dimensional plane is composed of square or rectangular pixels with side about 10 μm to 300 μm. Each pixel expresses a minimum unit of the X-ray image (FIG. 6).

It is preferable that the pixel size of the digital X-ray image detector 2 is 20 μm to 300 μm, and the more preferable is 50 μm to 200 μm. Further, concerning the size of the detecting surface of the digital X-ray image detector 2, the size of 15 cm×15 cm to 90 cm×90 cm can be used preferably for the medical service.

Here, it can happen that the peak and the trough caused by the edge effect are cancelled each other and the phase contrast edge-enhancement disappears, when the pixel size is larger than the above-mentioned EB or EP. Accordingly, it is preferable that the peak and the trough of the phase contrast edge-enhancement are away each other to be the pixel size or more, to detect the phase contrast edge-enhancement by the digital X-ray image detector 2. Even when the pixel size is larger than EB or EP, if the peak or the trough of the phase contrast edge-enhancement exists in the different pixel respectively, the phase contrast edge-enhancement can be detected. When the pixel size is larger than the distance between the peak and the trough, the peak and the trough are cancelled each other in the one pixel in one case, and the phase contrast edge-enhancement can be detected by seizing in the different pixels in the other case. That is, the phase contrast edge-enhancement can be detected by the probability theory, and the larger the distance between the peak and the trough is, comparing with the pixel size, the more easily the phase contrast edge-enhancement is detected.

In case that the Coolidge X-ray tube 5 is used, while the distance between the peak and the trough of the phase contrast edge-enhancement is expanded by the geometrical unsharpness, the difference between the height of the peak and the depth of the trough, or the intensity of the phase contrast edge-enhancement, becomes lower. Accordingly, if the distance between the peak and the trough is expanded by the geometrical unsharpness, the phase contrast edge-enhancement is detected most strongly, when the distance between the peak and the trough is nearly equal to the pixel size.

On the other hand, when using the parallel X-ray, when R2 becomes large, the edge width is expanded, and thereby, the X-ray intensity detected by the digital X-ray image detector 2 can be detected strongly, because the distance between the peak and the trough of the phase contrast edge-enhancement is larger than the pixel size.

As mentioned above, the intensity of the phase contrast edge-enhancement is determined by relative relation between the distance between the peak and the trough of the phase contrast edge-enhancement and the pixel size of the digital X-ray image detector 2, and changes continuously. Actually, its practical use area is obtained, when the distance between the peak and the trough is larger than 0.5 times the pixel size. Because, as a factor in which the phase contrast edge-enhancement expands to fall in out-of-focus, the other factor such as the out-of-focus caused by the detector itself, other than a diameter of focal spot of the X-ray tube, exists. In case of the Coolidge X-ray tube 5, the phase contrast edge-enhancement can be clearly observed, up to the distance between the peak and the trough of three times the pixel size, even when the X-ray intensity goes down. Since too much expansion of the edge width makes the image to be difficult for watching, the more preferable is up to about 1.5 times.

Further, in case of the parallel X-ray in the same manner as mentioned above, the distance between the peak and the trough is about 3 times the pixel size, and more preferably, 1.5 times is a preferable condition. That is, "the pixel size of the digital X-ray image detector is nearly equal to the half-width of the phase contrast edge-enhancement of the phase contrast X-ray image" means the pixel size that is 0.5 to 3 times EB or EP. Further EB or EP here, for medical image, is about 1 mm of a blood vessel to be watched, or 0.1 mm of small calcified portion in the breast. Further in case of non-destructive test, it is about a few μm width of a metallic wire, which can be obtained by formula (3) or (4).

As mentioned above, in case that the Coolidge X-ray tube 5 is used, while the distance between the peak and the trough of the phase contrast edge-enhancement is expanded by the geometrical unsharpness, the difference between the height of the peak and the depth of the trough, or the intensity of the phase contrast edge-enhancement, becomes lower. Accordingly, if the original phase contrast edge-enhancement is not sufficient, the detection is impossible. That is, the phase contrast edge-enhancement E1 that is before occurrence of the geometrical unsharpness, expressed by formula (5), is 12 μm to 300 μm, which is preferable.

$$E=2.3(1+R2/R1)^{1/3}\{R2\delta(2r)^{1/2}\}^{2/3} \qquad (5)$$

On the other hand, in case of the parallel X-ray, since the deterioration of the phase contrast edge-enhancement caused by the geometrical unsharpness does not exist, the above mentioned limitation does not occur.

Based on the above-mentioned structure, the digital image of the phase contrast X-ray image can be obtained easily. That is, the digital image of the phase contrast X-ray image having the higher sharpness can be obtained, by using the digital X-ray image detector such as the computed radiography (CR) or the flat type X-ray picture image detector (FPD) used widely in the medical field or the non-destructive test.

That is, it is possible to obtain the digital X-ray image having sharpness, enhanced in terms of the phase contrast edge by "the digital phase contrast X-ray radiographing system, wherein a pixel size of the digital X-ray image detector is nearly equal to a half-width of the phase contrast edge-enhancement of the phase contrast X-ray image".

Further, it is possible to obtain the medical diagnosis image having sharpness in general hospital facilities easily by "the digital phase contrast X-ray radiographing system wherein the X-ray tube in use is the Coolidge X-ray tube".

When the Coolidge X-ray tube is used, it is possible to obtain the medical diagnosis image having sharpness in general hospital facilities conveniently by "the digital phase contrast X-ray radiographing system wherein the digital X-ray image detector having a pixel size of 0.5 to 1.5 times EB value obtained by the following simulation formula".

$$EB=2.3(1+R2/R1)^{1/3}\{R2\delta(2r)^{1/2}\}^{2/3}+D\times(R2/R1)$$

Further, it is possible to obtain the X-ray image that describes the microscopic construction clearly by "the digital phase contrast X-ray radiographing system of the present invention wherein the X-ray in use is the radiation X-ray".

In case that the parallel X-ray is used, it is possible to obtain conveniently the X-ray image that describes the micro construction clearly by "the digital phase contrast X-ray radiographing system of the invention wherein a digital X-ray image detector having a pixel size of 0.5 to 1.5 times EP value obtained by the following simulation formula".

$$EP=2.3\{R2\delta(2r)^{1/2}\}^{2/3}$$

Further, it is possible to obtain the medical diagnosis image having sharpness by "the digital phase contrast X-ray radiographing system wherein E value obtained by the following simulation formula is not smaller than 12 μm and not larger than 300 μm".

$$E=2.3(1+R2/R1)^{1/3}\{R2\delta((2r)^{1/2}\}^{2/3}$$

[The Preferred Embodiment]

The examples of the embodiments of the digital phase contrast X-ray radiographing system of the present invention are shown in detail below, however the inventions are not limited to the embodiments.

The digital phase contrast X-ray radiographing system of the present invention is, as shown in FIGS. 1 to 6, the digital X-ray image detector composed of the X-ray source such as the radiation X-ray source or the Coolidge X-ray tube, and the two-dimensional flat face image detector of the X-ray image such as CR or FPD. The digital X-ray image obtained here is processed in image process 10 and CAD 11, shown in FIG. 7, and is printed as a transparent image X-ray film by a laser imager in image print output 12. Further, the digital X-ray image is displayed on image display 13 such as a cathode ray tube or a liquid display, or used for the purpose of an image diagnosis, after stored in image signal storage 14.

Figure 7:
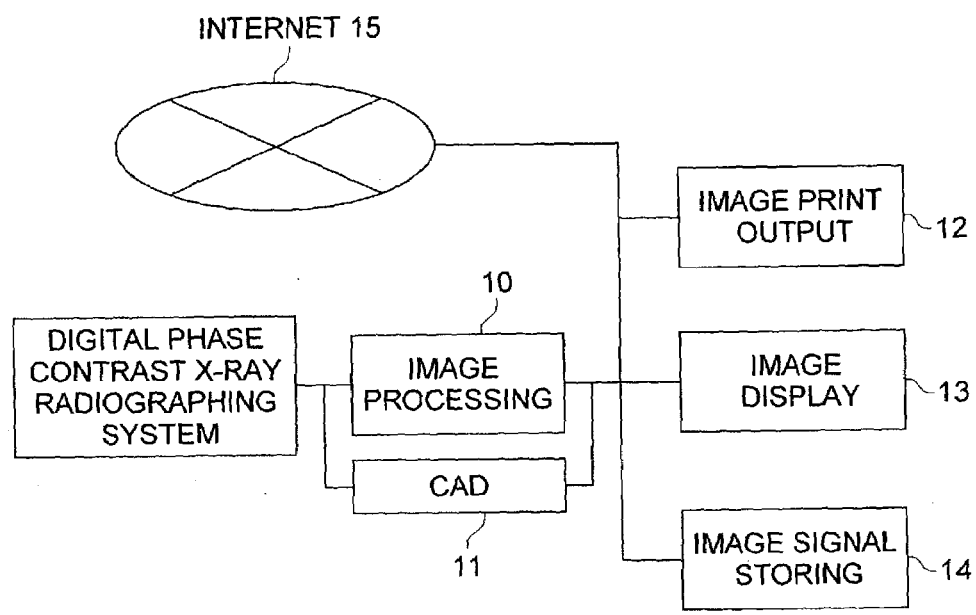
FIG. 7 is a drawing describing a usage of an output of a digital phase contrast X-ray radiographing system.

In the digital phase contrast X-ray radiographing system, the reduction or the enlargement of the image can be performed freely, further, a gradation process or a frequency process of the outputted image can be performed, because the digital X-ray image is obtained. Further, as shown in FIG. 7, an image forwarding to a distant place can be performed easily by Internet 15.

The reason why the Coolidge X-ray tube is called an electro-thermal X-ray tube is that there is an X-ray generating mechanism wherein a thermal electron radiated from a heated filament collides with a metallic anode to generate X-ray having energy corresponding to accelerating voltage. For the metallic anode, used are molybdenum, rhodium, tungsten, copper or silver. The metal used for the anode generates intense heat by the strong collision of the thermal electron, and melts. In order to dissolve the aforementioned inconvenience, the electro-thermal X-ray tube, having a rotating anode in which a disc type anode rotates, is widely used in the medical field. The X-ray tube having a fixed anode and the X-ray tube having rotating anode can be used in the present invention. Further, the present invention does not limit the type of the metal for the anode or the accelerating voltage. Generally, concerning non-destructive test or medical diagnosis radiography, the anode made of molybdenum, rhodium or tungsten, is used. Further, concerning the voltage for accelerating the thermal electron, the range of 10 kV to 200 kV is preferable. Since the setting voltage is the highest kinetic energy component of X-ray, the X-rays based on the set voltage individually are called X-ray of 20 kVp (kilo volt peak) or X-ray of 150 kVp.

When the electro-thermal X-ray tube is used, a window through which the X-ray is radiated is called a focal spot. The window is nearly square, and the length of a side is called a focal spot size. For the measuring method of this focal spot size, there are a pin-hall camera method, a slit camera method and a resolving power method, which are described in JIS 4704-1994. In the normal electro-thermal X-ray tube on the market, the makers measure the focal spot size by each method individually, and express the focal spot size as the product specification, which is general. Since accuracy is about ±15%, there is no problem, when this focal spot size is understood as the actual focal spot size of the X-ray tube.

The focal spot size of the X-ray tube used in the present invention is 10 μm to 500 μm preferably, and more preferably, it is 50 μm to 200 μm. The smaller the focal spot size is, the smaller component of the subject is described clearly, however, too small size does not create the X-ray having the sufficient intensity for penetrating the human body. Further, if the focal spot size is too large, the geometrical unsharpness turns out to be large, and the edge effect disappears.

The radiation X-ray is generated by the so-called synchrotron. When the electron is accelerated to the vicinity of the speed of light, and driven in a circular movement, a strong X-ray having a very small radiation angle in a tangential direction is generated. For example the radiation angle is less than 100 μm radian, which changes to 10 μm radian or a few μm radian, according to the speed of the accelerated electron. Characteristics of the radiation X-ray are that the radiation angle is small, or highly parallel, and a monochromatic X-ray having the sufficient intensity can be obtained by Bragg reflection of a silicon crystal due to the strong intensity. For example, the monochromatic X-ray having high energy of 17 keV or 50 keV that can sufficiently penetrate the human body can be generated, and the clear image capable of being used for the medical image diagnosis with a strong phase contrast edge-enhancement by refraction can be obtained.

The radiation X-ray is obtained by, for example, a synchrotron installed in High Energy Research in Tsukuba city, Ibaraki Prefecture, Japan, SPring-8 installed in Harima, Hyogo Prefecture, Japan, and a microtron disclosed in TOKUGAN 2000-366836. Since the obtained X-rays here are extremely parallel, there is no expansion of the X-ray though R2 is determined to be large, and there is no deterioration of X-ray intensity, accordingly, the half-width EP of the edge effect that is wide sufficiently can be determined.

When the radiation X-ray source is used, there is no need to determine the distance between the X-ray source and the subject particularly. Preferable is that the subject is located at a sufficiently safe place. However, when the electro-thermal X-ray tube is used, the distance (R1) between the X-ray tube and the subject is about 0.1 m to 2 m. Preferable is about 0.3 m to 1 m.

When the radiation X-ray source is used, the distance (R2) between the subject and the digital X-ray image detector is preferable for 0.15 m to 50 m. Too close distance cannot cause the effect of the phase contrast edge-enhancement sufficiently. Further, too far distance causes a physical limit to a radiographing room for use. Further, when the electro-thermal X-ray tube is used, the distance (R2) between the subject and the digital X-ray image detector is preferable for 1.5 m to 5 m. The reason why this limit is used is the same as the reason described above.

The smallest reading size of the subject in the present invention, or the smallest size about a size of pieces from which information of the subject is read, is about 30 μm to 10 mm, as a diameter of a column. There is required about 30 μm for non-destructive test. For mammography X-ray image, about 100 μm is required. Further, for a chest image, a range about 1 mm to 5 mm is required. The smallest reading size can be established in accordance with the subject.

The subject is a metal such as an iron or the human body. In this case, the value of δ is in the orders of $10^{-8}$ to $10^{-6}$.

The digital X-ray image detector 2 for the two-dimensional plane used in the present invention is a computed radiography: CR using a stimulable phosphor plate, a solid type imaging element such as a flat panel detector: FPD (a direct method, an indirect method), or one composed of a phosphor ($GD_2O_2S$: Tb, CsI), a lens (or a taper) and CCD.

When these digital X-ray image detectors 2 are used, the phase contrast image is an enlarged radiography, which corresponds to the one wherein the pixel size of the digital X-ray image detector 2 is reduced. That is, it corresponds to the performance of a highly precise reading, which has a merit that the image information increases.

When the radiation (such as X-ray, α-ray, β-ray, γ-ray, electron beam, or ultra-violet ray,) is radiated onto the stimulable phosphor plate, a part of the radiation energy is accumulated in the stimulable phosphor plate, and after that, when exciting light represented by visual light is radiated onto the stimulable phosphor plate, an accumulation type phosphor (that is the stimulable phosphor) performs stimulable phosphor radiation. Based on the above-mentioned principle of the stimulable phosphor, the stimulable phosphor plate can output the radiated image of the subject onto the recording material represented by photosensitive material or CRT as a visual image, accordingly the radiographed information of the subject such as the human body is once recorded on the sheet shaped accumulation type phosphor, and the accumulation type phosphor is scanned by the exiting light such as laser light, and due to this, the stimulably emitted light is generated, and the obtained stimulably emitted light is read out photoelectrically, and then the image signal is obtained (TOKKAISHOU 55-124929, 56-163472, 56-104645, 55-116340).

Further, as the solid type imaging element represented by a flat panel detector, as described in Japanese TOKKAIHEI 6-342098, such a method is used that a photoconductive layer generates electrical charges corresponding to the intensity of the radiated X-ray, and the generated electrical charge are accumulated in a plurality of capacitors which are arranged two-dimensionally. Further, as described in TOKKAIHEI 9-90045, there is also used a method wherein when X-ray is absorbed in the phosphor layer of the intensifying screen, a fluorescence is generated and the intensity of the fluorescence is detected by the detectors represented by photodiodes arranged in each of the pixels.

Concerning the above-mentioned solid type imaging element represented by a flat panel detector, it is possible to use a photo detector represented by the photodiode, or an organic flat panel detector wherein a switching element represented by TFT is manufactured by using an organic semiconductor.

Figure 8:
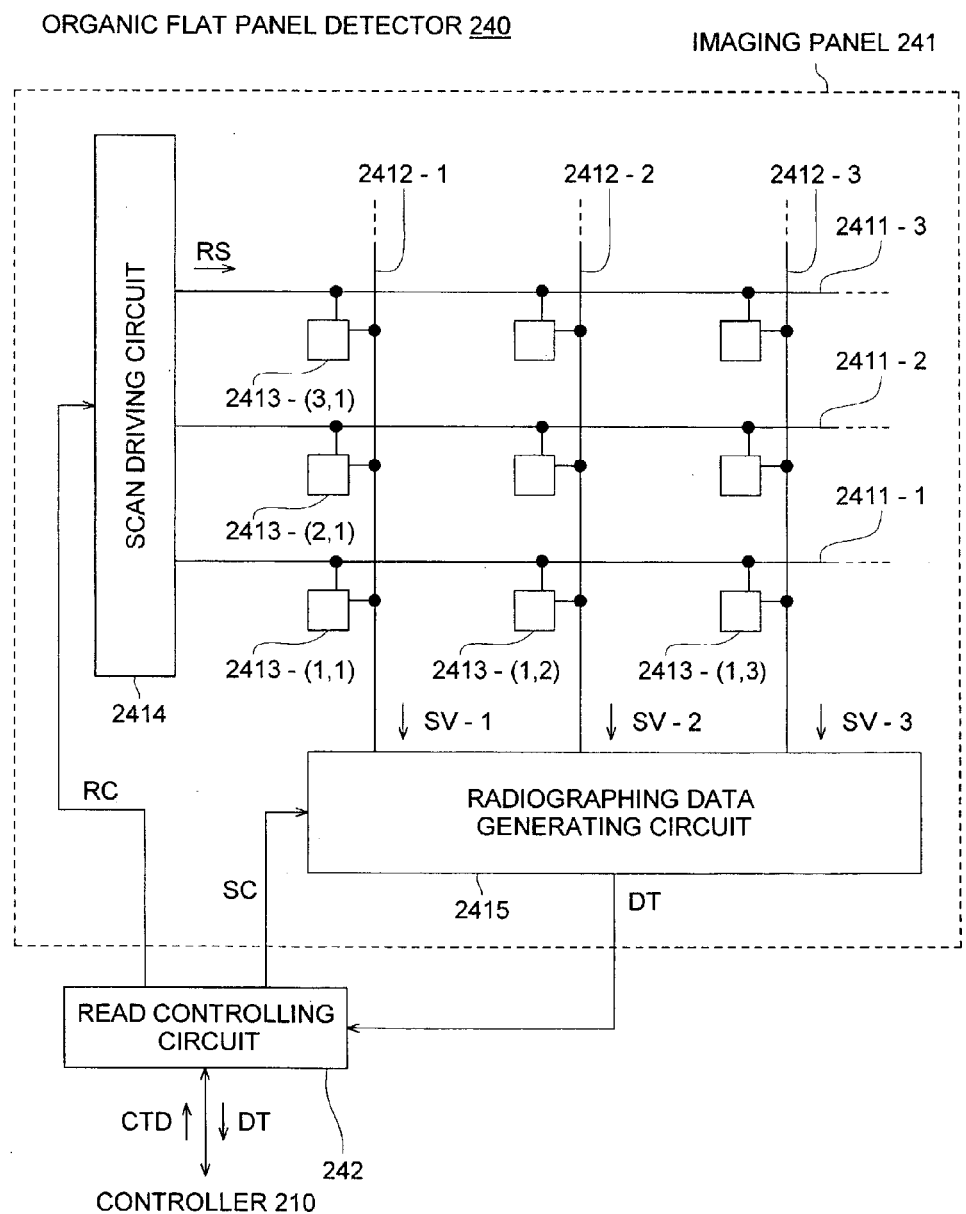
FIG. 8 is a drawing describing a structure of an imaging panel provided on a flat panel detector.

Here, imaging panel 241 provided in flat panel detector 240 will be described, referring to FIG. 8. This imaging panel 241 has a base plate having a thickness by which a predetermined rigidity is obtained, and detecting elements 2413-(1, 1) to 2413-(m, n) which output electric signal according to the amount of the radiation are arranged on this base plate two-dimensionally in a matrix type. Further, scanning-lines 2411-1 to 2411-m and signal lines 2412-1 to 2412-n are arranged to cross at right angles each other.

The scanning lines 2411-1 to 2411-m of the imaging panel 241 are connected to scan-driving section 2414. When read-out signal RS is supplied from the scan-driving section 2414 to one scanning line 2411-p (p is a value of either one of 1 to m) that is either one of the scanning lines 2411-1 to 2411-m, electric signals SV-1 to SV-n corresponding to the radiation amount are outputted from a detecting element that is connected to the scanning line 2411-p, and are supplied to radiographing data generating circuit 2415 through the signal lines 2412-1 to 2412-n.

The detecting element 2413 can be the one which outputs the electric signals corresponding to the radiated amount of the radiation. In case that the detecting element is composed of the photoconductive layer whose resistance value changes due to the generation of a paired electron-electron hole under the radiated radiation, the amount of electric charge corresponding to the amount of radiation generated in the photoconductive layer is accumulated in an electric charge accumulating capacitor, and the electric charge accumulated in the electric charge accumulating capacitor is supplied to radiographing data generating circuit 2415 as the electric signal. Incidentally, the photoconductive layer whose dark resistance value is the highest is desirable, and amorphous selenium, lead oxide, cadmium sulfide, mercuric iodide or an organic materials having photoconductivity (including a photoconductive polymer to which X-ray absorption compound is added) are used, and in particular, the amorphous selenium is desirable.

Further, when the detecting element 2413 is composed of a scintillator that generates the fluorescence when the scintillator is irradiated, it is also possible to arrange so that the electric signal, that is based on the fluorescence intensity generated by the scintillator, is generated, and is supplied to radiographing data generating circuit 2415.

In the radiographing data generating circuit 2415, electric signal SV, that is supplied based on output control signal SC from read control circuit 242 described later, is selected in sequence, and is converted to digital radiographing data DT. The digital radiographing data DT are supplied to the read control circuit 242.

The read control circuit 242 is connected to controller 210, and generates scan control signal RC and output control signal SC, based on control signal CTD that is supplied from controller 210. The scan control signal RC is supplied to scan driving section 2414, and read-out signal RS is supplied to scanning lines 2411-1 to 2411-m, based on the scan control signal RC.

Further, the output control signal SC is supplied to the radiographing data generating circuit 2415. For example, in case that the imaging panel 241 is composed of (m×n) pieces of the detecting elements 2413 mentioned above, the data depending on the electric signal SV from the detecting elements 2413-(1, 1) to 2413-(m, n) are to be data DP (1, 1) to DP (m, n), then, radiographing data DT are generated in order of data DP (1, 1), DP (1, 2), - - - DP (1, n), DP (2, 1), - - - DP (m, n), by the scan control signal RC and the output control signal SC from the read control circuit 242, and the radiographing data DT are supplied from radiographing data generating circuit 2415 to the read control circuit 242. Further, the read control circuit 242 performs the process to send the radiographing data DT to controller 210.

The radiographing data DT obtained in the flat panel detector 240 are supplied to the controller 210 through the read control circuit 242. Incidentally, when the image data obtained in radiation image reading device represented by the flat panel detector 240 are supplied to the controller 210, the supply of the image data processed by a logalithmic conversion can make the process of the radiographic image data in the controller 210 to be simple.

Figure 9:
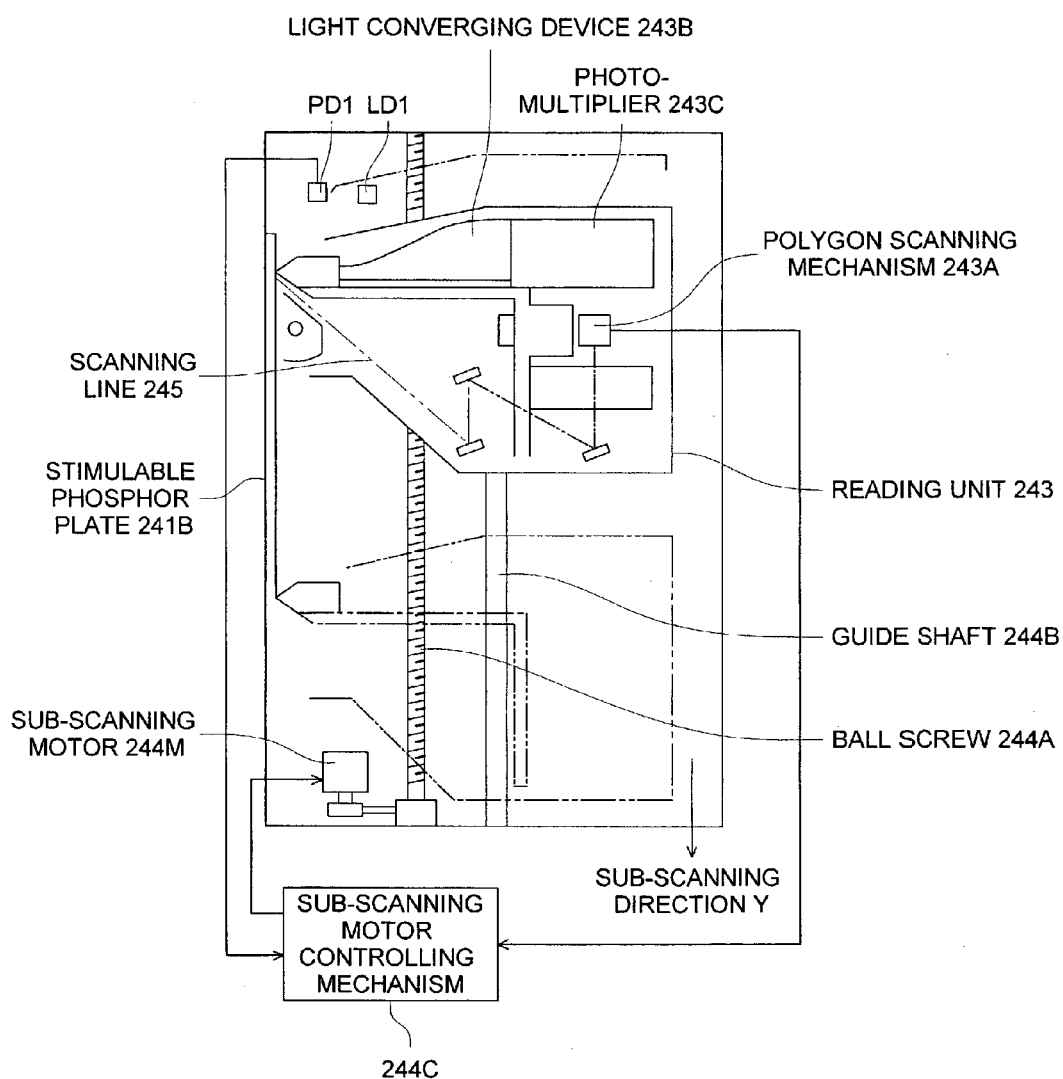
FIG. 9 is a drawing showing a mechanical section of a structural example of a flat panel detector in which a stimulable phosphor plate is used.

Next, the mechanical section of the structural example of the flat panel detector 240 composed of the stimulable phosphor plate will be shown in FIG. 9. Firstly the flat panel detector 240 will be described. Stimulable phosphor plate 241B is fixed on a left wall, and is used repeatedly. Reading unit 243 moves along guide shaft 244B by the drive of ball screw 244A connected to sub-scanning motor 244M composed of a stepping motor, and drives scanning line (light beam) 245 in the sub-scanning direction.

The scanning in the scanning direction is performed by polygon scanning mechanism 243A. The polygon scanning mechanism 243A includes a polygon and a mechanism to rotate the polygon. The movement of sub-scanning motor 244M is controlled by sub-scanning motor control mechanism 244C. The fluorescence is converged by light converging device 2431, and changed into an electric signal by photo-multiplier 243C.

Symbol LD1 is a laser light source, and symbol PD1 is a photo-sensor, which constitute an initial point detecting sensor. The initial point detecting sensor detects the initial point in the sub-scanning direction of the reading unit 243. Output of the photo-sensor PD1 is inputted to sub-scanning motor control mechanism 244C, and the sub-scanning motor control mechanism 244C controls a stopping position of the reading unit 243.

Incidentally, though there is shown the example in which the reading unit 243 is moved by the drive of the ball screw 244A, the one in which the stimulable phosphor plate 241B is moved in the sub-scanning direction can be also used.

For the detecting means for detecting the fluorescence, there is a method in which CCD and C-MOS sensor are used. Further, also used is a construction composed of an X-ray scintillator which radiates the visible light when irradiated by the X-ray, and an area sensor which corresponds to a lens-alley and each lens.

Still further, in an X-ray mass examination, for example, radiography is performed by using an ordinary X-ray film. In order to input these X-ray photographs in the system of the present embodiment, a laser digitizer is used. The foregoing is can be performed by scanning the film with a laser beam, measuring the transmitted light amount, and performing an A-D conversion of the obtained value, then it becomes possible to use the digital image data. The pixel size in this case corresponds to a sampling pitch of the laser digitizer.

In order to obtain the digital X-ray image by the above-mentioned various constructions, an effective pixel size of an image is less than 200 μm preferably, and in particular, less than 100 μm is preferable for a mammography, though it depends upon a radiographing region or a diagnosis purpose. Further, a density level of an image is more than 10 bits preferably, and in particular, more than 12 bits are preferable.

In digital X-ray image detector 2, the smallest read-out size of an imaging plate is a pixel size of a digital image in the case of CR, and it is preferable that the smallest read-out size is larger than 30 μm, and less than 300 μm. When it is smaller than 30 μm, the pixel number is enormous, which obstructs a quick image processing or image displaying. The more preferable is 50 μm to 200 μm. In the case of FPD, the smallest X-ray image detecting size is a pixel size, and a range from 30 μm to 300 μm is preferable as in the case of CR.

The optimum pixel size varies depending on the subjects. When the radiography is performed with two times magnification, the pixel size of about 100 μm is appropriate for the region such as a hand bone in which a fine component is included. Even when the pixel size is smaller than 100 μm, the amount of information hardly changes, and when the pixel size is larger than 100 μm, image information is lower and deteriorated. Since there are few fine components in a chest image, as compared with that of the hand bone image, there is no deterioration of image information, as far as the pixel size is not greater than 200 μm. On the other hand, very fine information of micro calcified portion is necessary for a breast image, and thereby, the pixel size of less than 100 μm is necessary, and the better image is obtained by the pixel size of 50 μm.

The digital image signal of the phase contrast edge-enhanced image is image-processed appropriately and displayed on the monitor, or is formed to a hard copy by a printer. As for the size of the object to be observed, it is very important to watch the object using a real size, for example, in the medical service. Accordingly, a preferable manner is to display the real size on the monitor or the hard copy, and further, in order to check the image precisely, the enlargement of the image to the optional size is also the preferable manner. Still further, it is the preferable manner that image information is changed to an electronic signal to be stored after it is used for the image diagnosis.

The digital phase contrast X-ray radiographing system of the present invention can be used for medical image diagnosis, medical sample image diagnosis, and the inspection of IC chips for the industrial use.

EXAMPLE

1. Simulation calculation in the case of using the Coolidge X-ray tube.

Figure 10:
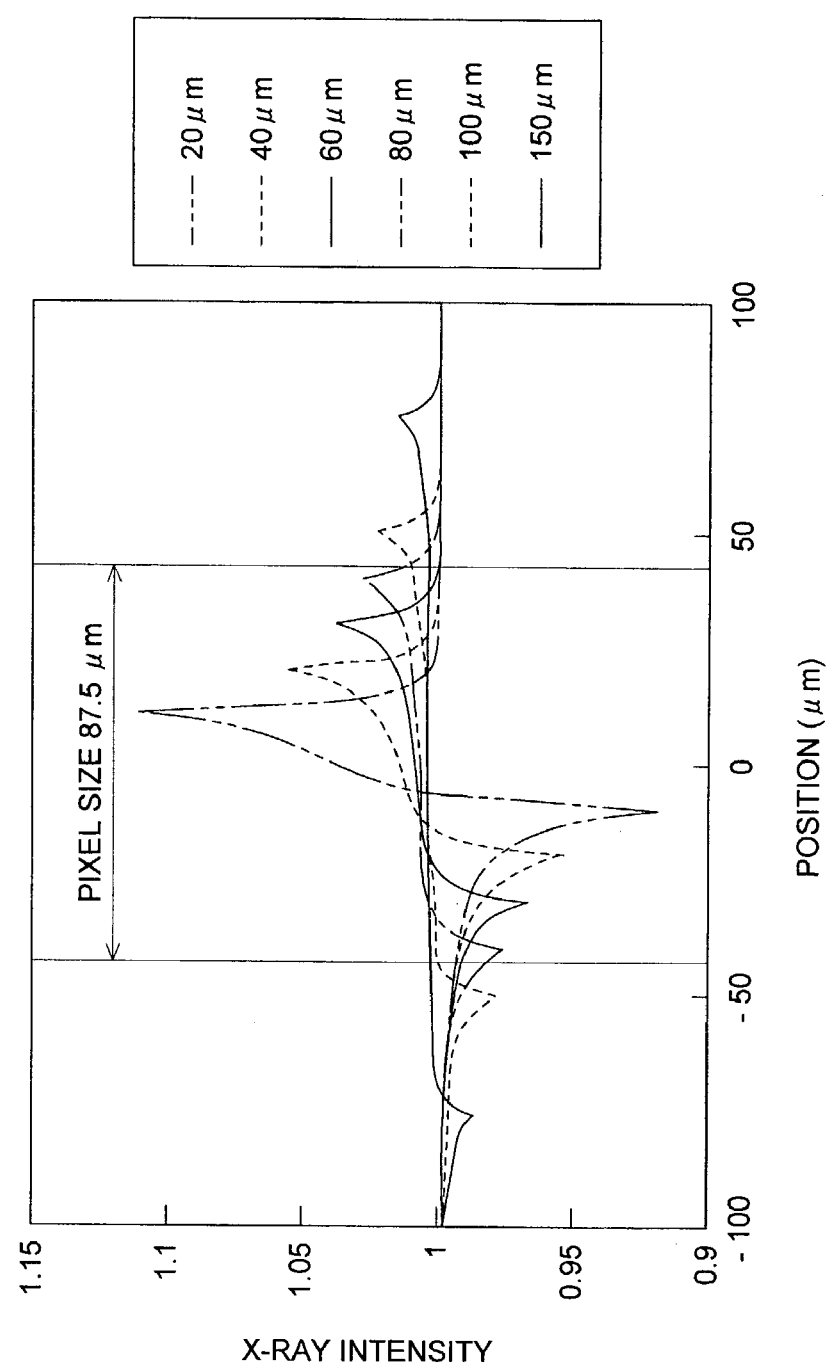
FIG. 10 is a drawing showing a result when a focal spot size of X-ray tube is changed from 20 μm to 150 μm.

The subject was a plastic fiber having a diameter of 1 mm. When X-ray energy was 50 keV, δ was shown by $\delta=8\times10^{-7}$. Under the condition of R1=1 m, and R2=1 m, an edge profile on the digital X-ray image detector of the Coolidge X-ray tube was calculated by formula (3). When the size of the focal spot of the X-ray tube was changed from 20 μm to 150 μm, the result is shown in FIG. 10. The larger the focal spot size is, the lower the edge intensity is, and the wider the edge width is. In case that the pixel size is 87.5 μm, the peak and the trough of the phase contrast edge-enhancement is out of the pixel respectively, when the focal spot size is 100 μm. That is, when the X-ray tube having the focal spot size of 100 μm is used, it is understood that the highest phase contrast edge-enhancement is obtained strongly among the simulation calculation.

2. Experimental result of radiography using the Coolidge tube.

X-ray tube L6622-02 having a tungsten anode made by Hamamatusu Photonix was used. The focal spot size was 100 μm, and tube voltage was set to 50 keV. A 200 μm-thick polyester base plate was used as a holding bracket, and a columnar resin having diameter of 1 mm was made to be a subject. REGIUS Plate RP-1S (35 cm×43 cm), representing a stimulable phosphor plate, made by Konica, was used for the digital X-ray image detector. Distances R1 and R2 were set for the radiography as shown in Table 1. Radiographing condition was set to 10 mAs for R1=R2=1 m. When the distance is changed, X-ray radiograph is performed by adjusting the X-ray radiating amount so that an amount of X-ray irradiated on the subject is constant. REGIUS 150, made by Konica, having stimulable phosphor plate, was used for reading image information for each radiographing.

The reading size in this case was 87.5 μm. The read-out image data were printed on a silver halide photographic film for recording use by Laser Imager Li62P made by Konica. After the developing process of the photographic film, the image on the photographic film was observed on a viewing box of 8,000 lx. It was decided that mark C means no edge-enhancement on the edge of the subject or too much edge-enhancement with incongruity, mark B means visual edge-enhancement, and mark A means sufficient visual edge-enhancement. The results are shown in Table 1.

TABLE 1

| Sample No. | R1 (m) | R2 (m) | Evaluation of edge effect | EB calculated value (μ) | E calculated value (μ) | Remarks |
|---|---|---|---|---|---|---|
| 1 | 1.20 | 1.20 | A | 128 | 28 | Present invention |

TABLE 1-continued

| Sample No. | R1 (m) | R2 (m) | Evaluation of edge effect | EB calculated value (μ) | E calculated value (μ) | Remarks |
|---|---|---|---|---|---|---|
| 2 | 1.00 | 1.00 | A | 125 | 25 | Present invention |
| 3 | 0.60 | 0.60 | B | 118 | 18 | Present invention |
| 4 | 0.30 | 0.30 | C | 111 | 11 | Comparison |
| 5 | 1.00 | 0.50 | B | 64 | 14 | Present invention |
| 6 | 0.60 | 0.30 | C | 60 | 10 | Comparison |
| 7 | 1.00 | 0.25 | C | 33 | 8 | Comparison |
| 8 | 1.00 | 2.50 | C | 305 | 55 | Comparison |

3. Simulation calculation in the case of using the parallel X-rays.

The subject is a plastic fiber having a diameter of 1 mm. When X-ray energy is 50 kev, δ is shown by $\delta=8\times10^{-7}$. By using CR having pixel size of 87.5 μm, R2 is obtained for observing the phase contrast edge-enhancement sufficiently. Since there is no deterioration of edge intensity due to the geometrical unsharpness of the diameter of the focal spot in case of parallel X-rays, R2 is obtained to be 9.3 m, as EP value of 87.5 μm. From this calculation, when the imaging plate is nearly 5 m or more away from the subject, the edge of 1 mm fiber starts to be observed, and the edge effect due to the phase contrast can be clearly obtained, at the distance of 10 m.

EFFECT OF THE INVENTION

As mentioned above, Structures (1) to (8) can obtain the digital image of the phase contrast X-ray image conveniently, that is, the digital X-ray phase contrast image having high image sharpness is easily obtained, by using the computed radiography (CR) or the digital X-ray image detector such as a flat type X-ray picture image detector (FPD), which is used in medical service or in non-destructive test widely.

What is claimed is:

1. An X-ray image radiographing system for radiographing a subject, comprising:
an X-ray source to emit X-rays;
a digital X-ray detector to detect a digital X-ray image of the subject, wherein the subject is placed between the X-ray source and the digital X-ray detector in an arrangement to satisfy the following formulas so that an edge of the digital X-ray image is enhanced over an edge-enhanced width on which image contrast is sharply changed:

$0.1 \text{ m} \leq R1 \leq 10 \text{ m, and } 0.15 \text{ m} \leq R2 \leq 10 \text{ m,}$ where R1 is a distance between the X-ray tube and the subject and R2 is a distance between the subject and the digital X-ray detector;

wherein the digital X-ray detector is a Coolidge X-ray tube having a size D of focal spot defined by the following formula of $10 \text{ μm} \leq D \leq 500 \text{ μm}$, and wherein R1 is (D-7)/200 (m) or more, and wherein the digital X-ray detector has a pixel size of from 20 μm to 300 μm and the pixel size is 0.5 to 3 times an EB value which represents the half width of the edge-enhanced width and is obtained by the following simulation formula:

$EB=2.3(1+R2/R1)^{1/3}\{R2\delta(2r)^{1/2}\}^{2/3}+D\times(R2/R1)$ where δ is represented by the following formula of $\delta=1-n$ (n is a refractive index of an X-ray).

2. The X-ray image radiographing system of claim 1, wherein the following formulas are satisfied:

$0.3 \text{ m} \leq R1 \leq 2 \text{ m, and } 0.2 \text{ m} \leq R2 \leq 2 \text{ m.}$ 3. The X-ray image radiographing system of claim 1, wherein the following formulas is satisfied:

$50 \text{ μm} \leq D \leq 300 \text{ μm.}$

4. The X-ray image radiographing system of claim 1, wherein the digital X-ray detector has a detecting surface having a size of (15 cm×15 cm) to (90 cm×90 cm).

5. The X-ray image radiographing system of claim 4, wherein the detecting surface has a size of (15 cm×15 cm) to (50 cm×50 cm).

6. The X-ray image radiographing system of claim 4, wherein the pixel size is 50 μm to 200 μm.

7. An X-ray image radiographing system for radiographing a subject, comprising:
an X-ray source to emit X-rays;
a digital X-ray detector to detect a digital X-ray image of the subject, wherein the subject is placed between the X-ray source and the digital X-ray detector in an arrangement to satisfy the following formulas so that an edge of the digital X-ray image is enhanced over an edge-enhanced width on which image contrast is sharply changed:

$0.1 \text{ m} \leq R1 \leq 10 \text{ m, and } 0.15 \text{ m} \leq R2 \leq 10 \text{ m,}$ where R1 is a distance between the X-ray tube and the subject and R2 is a distance between the subject and the digital X-ray detector;

wherein the X-ray is a radiation X-ray, and wherein the digital X-ray detector has a pixel size of from 20 μm to 300 μm and the pixel size is 0.5 to 3 times of an EP value which represents the half width of the edge-enhanced width and is obtained by the following simulation formula:

$EB=2.3\{R2\delta(2r)^{1/2}\}^{2/3}$ where δ is represented by the following formula of $\delta=1-n$ (n is a refractive index of an X-ray).

* * * * *